US010736789B2

(12) United States Patent
Cree

(10) Patent No.: US 10,736,789 B2
(45) Date of Patent: Aug. 11, 2020

(54) ABSORBENT ARTICLE WITH MICROENCAPSULATED PHASE CHANGE MATERIAL

(71) Applicant: First Quality Retail Services, LLC, Great Neck, NY (US)

(72) Inventor: James William Cree, Loveland, OH (US)

(73) Assignee: First Quality Retail Services, LLC, Great Neck, NY (US)

( * ) Notice: Subject to any disclaimer, the term of this patent is extended or adjusted under 35 U.S.C. 154(b) by 675 days.

(21) Appl. No.: 15/424,066

(22) Filed: Feb. 3, 2017

(65) Prior Publication Data

US 2017/0360620 A1    Dec. 21, 2017

Related U.S. Application Data

(60) Provisional application No. 62/350,433, filed on Jun. 15, 2016.

(51) Int. Cl.
*A61F 13/15* (2006.01)
*A61F 13/84* (2006.01)
(Continued)

(52) U.S. Cl.
CPC .. *A61F 13/15203* (2013.01); *A61F 13/51121* (2013.01); *A61F 13/5376* (2013.01);
(Continued)

(58) Field of Classification Search
CPC .......... A61F 13/15203; A61F 13/51121; A61F 13/53747; A61F 2013/5113; A61F 2013/530802
See application file for complete search history.

(56) References Cited

U.S. PATENT DOCUMENTS

| 5,677,048 A | 10/1997 | Pushaw |
| 5,804,297 A | 9/1998 | Colvin et al. |
| 6,120,487 A * | 9/2000 | Ashton ............. A61F 13/49009 604/358 |

(Continued)

FOREIGN PATENT DOCUMENTS

| AU | 2009252869 B2 | 5/2014 |
| CN | 101302664 A | 11/2008 |

(Continued)

OTHER PUBLICATIONS

International Search Report of the International Searching Authority relating to International Application No. PCT/US2017/16443, dated Apr. 21, 2017.

(Continued)

*Primary Examiner* — Jacqueline F Stephens
(74) *Attorney, Agent, or Firm* — Amster, Rothstein & Ebenstein LLP

(57) ABSTRACT

An absorbent article is provided with microencapsulated phase change material (microPCM) particles that are embedded in and/or coated onto a layer of the absorbent article that includes a resilient sheet of an open-cell foam. The foam layer is disposed such that it is in contact with or is in proximity to the user. The microPCM particles absorb heat generated during use of the absorbent article to reduce the contact temperature on the inside of the absorbent article and improve the comfort of the user. To maximize comfort, the phase change temperature of the microPCM particles may be an average normal body temperature.

18 Claims, 2 Drawing Sheets

(51) Int. Cl.
*A61F 13/537* (2006.01)
*A61F 13/511* (2006.01)
*A61F 13/53* (2006.01)

(52) U.S. Cl.
CPC .... *A61F 13/53747* (2013.01); *A61F 13/8405* (2013.01); *A61F 2013/5113* (2013.01); *A61F 2013/530802* (2013.01)

(56) References Cited

U.S. PATENT DOCUMENTS

| | | | |
|---|---|---|---|
| 6,989,471 | B2 | 1/2006 | Schmidt et al. |
| 8,404,345 | B2 | 3/2013 | Naylor Rocha Gomes et al. |
| 2006/0024486 | A1 | 2/2006 | Pause |
| 2006/0161122 | A1 | 7/2006 | Erdman et al. |
| 2009/0088719 | A1 | 4/2009 | Driskell |
| 2009/0157153 | A1 | 6/2009 | Lemke et al. |
| 2012/0138275 | A1* | 6/2012 | Biggin ............... C08J 9/0004 165/104.34 |

FOREIGN PATENT DOCUMENTS

| | | |
|---|---|---|
| CN | 102068715 B | 8/2013 |
| CN | 103806285 A | 5/2014 |
| CN | 204016621 U | 12/2014 |
| CN | 204379555 U | 6/2015 |
| EP | 1196053 B1 | 1/2007 |
| KR | 2006110492 A | 10/2006 |
| KR | 2004405580000 Y1 | 6/2008 |
| KR | 2010126618 A | 12/2010 |

OTHER PUBLICATIONS

Written Opinion relating to International Application No. PCT/US2017/16443, dated Apr. 21, 2017.
Pages from website of Microtek Laboratories—Microencapsulation Technology, printed Apr. 11, 2016; 56 pp. http://www.microteklabs.com/.

* cited by examiner

ABSORBENT ARTICLE WITH MICROENCAPSULATED PHASE CHANGE MATERIAL

CROSS-REFERENCE TO RELATED APPLICATIONS

This application claims the benefit of and priority to U.S. Provisional Patent Application Ser. No. 62/350,433, filed Jun. 15, 2016, the entire contents of which are incorporated by reference herein.

FIELD

The present invention generally relates to an absorbent article with microencapsulated phase change material (microPCM) particles.

BACKGROUND

A user of a conventional disposable absorbent article typically experiences a localized build up of heat that is generated by the body in the vicinity of the absorbent article. The heat, in turn, leads to increased trans-epidermal water loss (TEWL) as the user's body tries to diffuse the heat. The heat in the vicinity of the absorbent article is more noticeable during hot and humid weather, when a user who wears an absorbent article is performing extended physical activity, such as walking or running or when the user is committed to remain in an environment, such as a bed or chair, that generates heat. The friction caused by the absorbent article against a user's skin in combination with the TEWL that is induced by the heat can be a precursor to skin irritation and a breakdown of the skin barriers. If not quickly remediated, the friction and TEWL may lead to the formation of pressure ulcers that can cause irreversible damage to the skin of the user.

Some conventional absorbent articles include microporous breathable films to alleviate heat generated by use of the absorbent article. Microporous films enable air to flow through the absorbent article to reduce the humidity and, to a certain degree, the occlusion of the user's skin and pores. However, such films are incapable of cooling directly or indirectly the epidermis of a wearer of the absorbent article. Moreover, the effectiveness of the microporous films is dependent upon having a relatively cool environment surrounding the exterior of the absorbent article.

SUMMARY

An object of the present invention is to provide an absorbent article that is more effective than conventional absorbent articles in cooling a user in a hot environment.

An absorbent article according to an exemplary embodiment of the present invention has at least one layer that includes a foam ("foam layer") with microencapsulated phase change material (microPCM) particles embedded in the foam layer and/or coated on the foam layer. The foam layer thus serves as a carrier for the microPCM particles. The foam layer used in the present invention is a resilient sheet of an open-cell foam having at least one of a polyether urethane foam, a polyester urethane foam, a foam rubber, or a high internal phase emulsion polyethylene foam. The microPCM particles maintain a contact temperature of the absorbent article at or near a phase change temperature of the microPCM particles, when a user comes into contact with or in close proximity to the absorbent article. In a preferred embodiment, the phase change temperature of the microPCM particles that are used in the absorbent article corresponds to an average normal body temperature in the range of 98° F. to 99° F. (36° C. to 38° C.), and more preferably 98.6° F. (37° C.). Thus, in a preferred embodiment, the microPCM particles moderate the contact temperature of the absorbent article to a target temperature that is cooler to the touch, typically by 1 or 2° F., and more comfortable to the skin of a user of the absorbent article.

In at least one embodiment, the foam layer of the absorbent article is liquid permeable.

In at least one embodiment, the resilient sheet is substantially rectangular.

In at least one embodiment, the foam layer is a topsheet, an acquisition layer, an absorbent core, or is a combination of two or more selected from the group consisting of a topsheet, acquisition layer and an absorbent core.

In at least one embodiment, the absorbent article includes both a topsheet and an acquisition layer, and the foam layer is positioned between the topsheet and the acquisition layer.

In at least one embodiment, the absorbent article includes both a topsheet and an absorbent core, and the foam layer is positioned between the topsheet and the absorbent core.

In at least one embodiment, the microPCM particles are embedded in and/or coated onto less than the entirety of the foam layer.

In at least one embodiment, the microPCM particles are made of paraffin wax that is encapsulated in an olefinic hard shell.

In at least one embodiment, the microPCM particles are embedded in or coated onto the foam layer as an emulsion.

In an exemplary embodiment, an absorbent article includes from top to bottom a topsheet, a layer that includes a resilient sheet of an open-cell foam having at least one of a polyether urethane foam, a polyester urethane foam, a foam rubber, or a high internal phase emulsion polyethylene foam, an absorbent core, and a backsheet, wherein the foam layer includes microPCM particles embedded in and/or coated onto the foam layer, such as with a carrier emulsion.

In an exemplary embodiment, the absorbent article is a diaper, underwear, a sanitary napkin, an incontinence product, or a hygienic product.

Other features and advantages of the present invention will become readily apparent from the following detailed description and the accompanying drawings.

BRIEF DESCRIPTION OF THE DRAWINGS

The above and related objects, features and advantages of the present invention will be more fully understood by reference to the following, detailed description of the preferred, albeit illustrative, embodiment of the present invention when taken in conjunction with the accompanying figures, wherein.

DETAILED DESCRIPTION

The present invention is directed to an absorbent article, such as a disposable absorbent article, that includes at least one foam layer that includes foam with microPCM particles. The foam layer moderates the contact temperature of a surface of the absorbent article so that the temperature at the point of contact with or in proximity to a user's skin does not rise, or rises minimally. As a result, a user will not feel hot and TEWL will be mitigated when using the absorbent article. In an exemplary embodiment, the foam layer is a resilient sheet of an open-cell foam having at least one of a polyether urethane foam, a polyester urethane foam, a foam rubber, or a high internal phase emulsion polyethylene foam. As used herein, an "open-cell foam" refers to a foam material wherein the gas pockets connect with each other and the open-cell foam has a pore size that makes the foam liquid permeable.

As used herein, the term "absorbent article" refers to an article which absorbs and contains fluids and solid materials. For example, absorbent articles may be placed against or in proximity to the body to absorb and contain the various exudates discharged by the body. Absorbent articles may be articles that are worn, such as baby diapers, adult protective underwear and incontinence products, and feminine care products such as sanitary napkins, or hygienic products that are used to absorb fluids and solid materials, such as for the medical profession which uses products like disposable gowns and underpads. The term "disposable" is used herein to describe absorbent articles which are not intended to be laundered or otherwise restored or reused as an absorbent article, but instead are intended to be discarded after a single use and, preferably, to be recycled, composted or otherwise disposed of in an environmentally compatible manner.

As used herein, the term "phase change material" or "PCM" refers to a substance that can be used to maintain a target temperature over a period of time by storing heat within or releasing heat from the PCM. The heat exchange generally involves a change in phase between a liquid and a solid. When a solid PCM absorbs heat, the PCM acts as a heat sink while the solid PCM turns into its liquid phase. When the PCM encounters a cooler temperature, the PCM releases the stored heat and turns back into a solid. A PCM can provide its cooling (or heating) effect for a particular length of time, which depends on the enthalpy of melting of the PCM and is typically measured in Joules/gram. The total enthalpy depends primarily on the amount of PCM present, the external temperature, the physical configuration of the PCM as it is applied, such as in a thick or thin layer, and the thermal conductivity of the materials to which the PCM is applied. A microPCM particle is an encapsulated particle of PCM.

Figure 1:
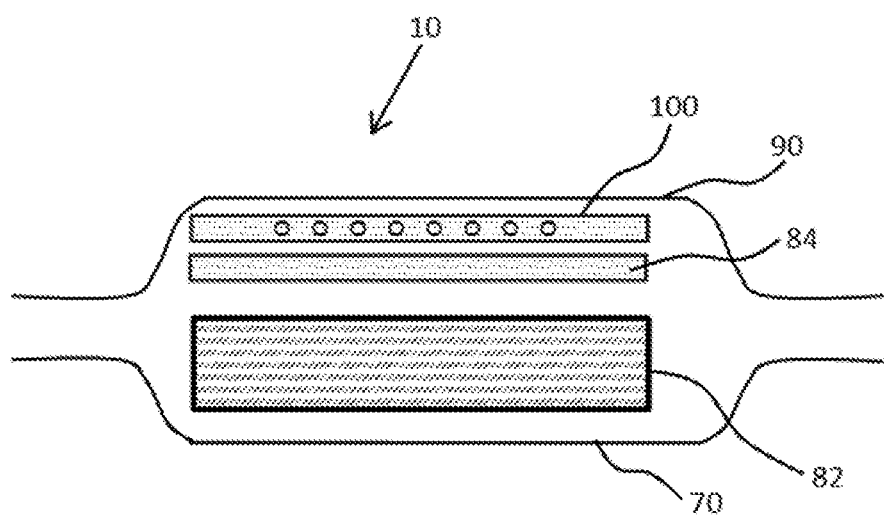
FIG. 1 is a cross-sectional view of a chassis of an absorbent article where microPCM particles have been embedded into and/or coated onto a foam layer that is included between a topsheet and an acquisition layer in accordance with an exemplary embodiment of the present invention.

FIG. 1 illustrates a cross-sectional view of a chassis of an absorbent article, generally designated by reference number 10, in accordance with an exemplary embodiment of the present invention. The absorbent article 10 includes a chassis made up of a backsheet 70, a topsheet 90, an absorbent core 82 that is disposed between the backsheet 70 and topsheet 90, an acquisition/distribution layer ("ADL") 84 that is disposed between the absorbent core 82 and the topsheet 90, and a foam layer 100 that contains microPCM particles. The foam layer 100 is disposed between the topsheet 90 and acquisition layer 84 to position the microPCM particles in proximity to a user's skin. (The absorbent core 82 and ADL 84 may or may not be limited to the crotch portion of the chassis.) The foam layer 100 is preferably liquid permeable so that liquid can pass through to acquisition layer 84 and absorbent core 82. In an alternative exemplary embodiment (not shown) where no acquisition layer is present, the foam layer 100 may be disposed between topsheet 90 and absorbent core 82. The microPCM particles may be embedded into and/or coated onto the foam layer 100 as, for example, an emulsion so that the microPCM particles do not come loose from the foam layer 100.

It may also be particularly useful for the microPCM particles to be applied to a resilient sheet of an open-cell foam that is inserted into portions of the absorbent article other than the chassis that come into frequent contact with the user. For example, microPCM particles may be embedded within and/or coated onto a resilient sheet of an open-cell foam that is included in the side panels or in the front or back waistband of a diaper or training pant.

While microPCM particles are designed to have one of multiple possible phase change temperatures, in the present invention, the microPCM particles preferably have a phase change temperature that corresponds to the average normal body temperature, e.g., approximately in the range of 98° F. to 99° F. (36° C. to 38° C.), and more preferably 98.6° F. (37° C.). One preferred type of microPCM particles is sold as product MPCM 37D by Microtek Laboratories, Inc. of Dayton, Ohio MPCM 37D contains encapsulated paraffin wax. The inclusion of microPCM particles with a phase change temperature that corresponds to the average normal body temperature provides a self-cooling system that can maintain or reduce the temperature on the inside surface of the absorbent article. Should the user's skin exceed the average normal body temperature, the phase change material will absorb the excess heat, thereby cooling the user.

The microPCM particles may lower the contact temperature of the absorbent article so that it is cooler to the touch, typically by about 1° F. or 2° F. This temperature difference, especially in a humid environment, can substantially impact the comfort of the user as both humidity and temperature impact the comfort level of a worn absorbent article. For example, an ideal comfort range for an absorbent article may lie within the range of between 88° F. and 91° F. and between 40% and 50% RH (relative humidity). Outside of the ideal range, an increase or decrease of the temperature by just 1° F. may cause discomfort for a typical user. A 2° F. variation can have even more pronounced impact on user comfort.

In the present invention, topsheet 90 may be made of any suitable relatively liquid-permeable material currently known in the art or later discovered that permits passage of a liquid therethrough. For an absorbent article that is worn, the topsheet 90 typically comes in contact with the skin of the wearer, and is preferably made of a material that is gentle to human skin. Examples of suitable topsheet materials include nonwoven, spun-bonded or carded webs of polypropylene, polyethylene, nylon, polyester and blends of these materials, or perforated, apertured or reticulated films, and the like. Nonwoven materials are exemplary because such materials readily allow the passage of liquids to the underlying acquisition/distribution layer 84, and therethrough to absorbent core 82. The topsheet 90 is preferably formed of a single ply of nonwoven material that may be made of fibers including polypropylene, polyethylene, polyethylene terephthalate (PET), polylactide (PLA), nylon, polyester and blends of these materials which have been thermally bonded, spunbonded, spunlaced, hydroentangled, or a combination thereof, or a composite of nonwoven material, such as a spunbond-meltblown-spunbond (SMS) nonwoven. For example, the nonwoven material may have a basis weight of about 8-30 grams per square meter and have appropriate strength and softness for use as a topsheet in an application which will be in contact with human skin. Topsheet 90 may be treated with a surfactant, over the whole surface or a portion of the surface, rendering it hydrophilic to facilitate the passage of moisture through topsheet 90 and into the acquisition/distribution layer 84 and the absorbent core 82.

Acquisition/distribution layer 84 may be a single layer or multiple layers made of liquid-permeable synthetic or natural material, or a combination of both, or a single multilayer apertured film. Acquisition/distribution layer 84 serves to quickly collect and distribute discharged body fluid to absorbent core 82. Because such fluid is typically discharged in gushes, the area of absorbent core 82 proximate to the point of fluid discharge may be overwhelmed by its rate, resulting in a leak. Therefore, the acquisition/distribution layer 84 facilitates transport of the fluid from the point of discharge across its surface area to contact other parts of absorbent core 82 from which it can be more readily absorbed. The use of an acquisition/distribution layer is well known in the art. Accordingly, acquisition/distribution layer 84 of the absorbent article 1 may have any well known or as yet undiscovered construction.

Absorbent core 82 may be any absorbent material which is capable of absorbing and retaining liquids such as urine and certain other body exudates to help prevent the liquid from either rewetting the wearer or otherwise leaking out of the absorbent article. The absorbent material may generally be compressible, conformable to the shape of the wearer's body and should not impede normal movement by the wearer. The absorbent core 82 may be manufactured in a wide variety of sizes and shapes, (e.g., rectangular, hourglass, "T"-shaped, asymmetric, etc.) and from a wide variety of liquid-absorbent materials commonly used in disposable diapers and other absorbent articles. Examples of suitable absorbent materials include wood pulp fluff, creped cellulose wadding, meltblown polymers, chemically stiffened, modified or cross-linked cellulosic fiber, tissue including tissue wraps and tissue laminates, absorbent foams, absorbent sponges, superabsorbent polymers (SAP), absorbent gelling materials, or any similar absorbent material or combinations of materials.

Backsheet 70 may be made of a liquid-impermeable material or be comprised of multiple layers in which at least one layer is liquid-impermeable.

The following example illustrates the superior results that are achieved by including microPCM particles on a foam layer.

Example 1

Figure 2:
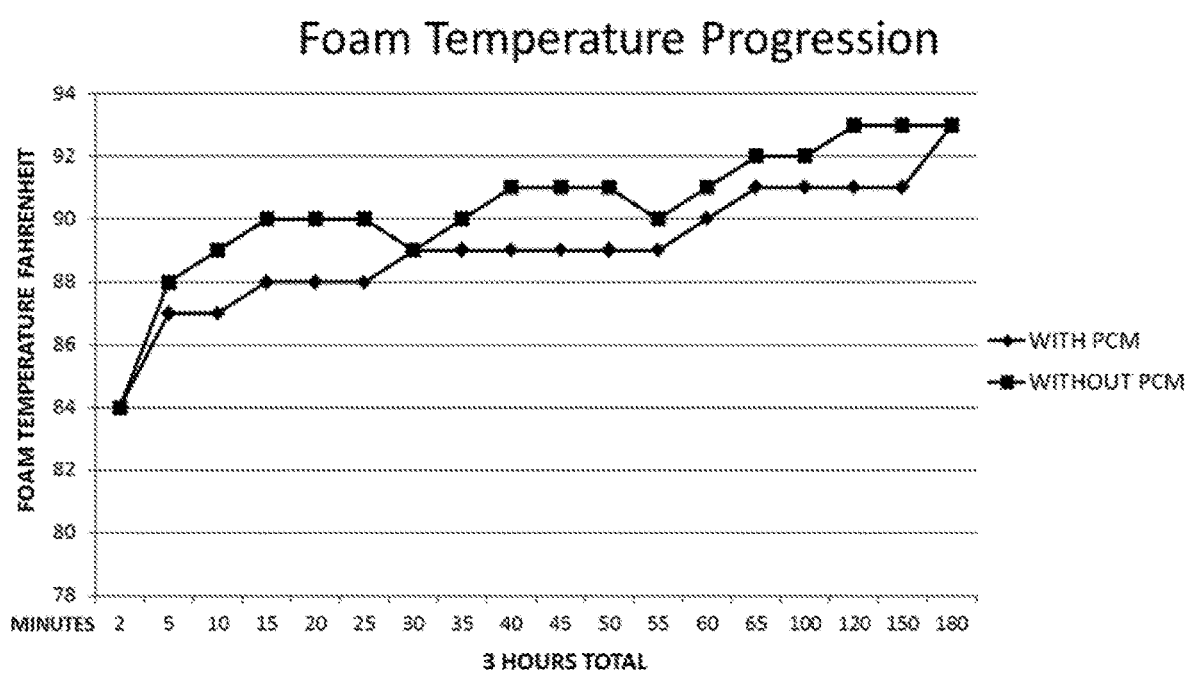
FIG. 2 is a graph showing the temperature over time of two pieces of absorbent open cell foam that are heated, where one piece of foam is treated with microPCM particles and the other piece of foam is not treated with the microPCM particles.

In this example, two pieces of absorbent open cell foam, as sold by the Peterson Chemical Company (Peterson Chemical Technology, Inc. 3300 Bee Caves Road, Suite 650 Austin, Tex. 78746) under the tradename CoolFlow™ were obtained for evaluation. One piece of CoolFlow™ foam was treated with a loading of PCM gels that encapsulate microPCM particles, where the PCM gels constituted approximately 10-20% by weight of the foam. The PCM gels had a temperature activation characteristic close to the average normal body temperature. The other piece of foam was not treated with PCM gels. The two foams, including the PCM-treated foam and the untreated foam, were then put in an oven that simulated the temperature of the body at approximately 98° F. for a period of 3 hours. The surface temperature of the foams was recorded at 5 minute intervals using a commercially available handheld infrared thermometer gun, Model GM320, available from Shenzhen Jumaoyuan Science And Technology Co., Ltd, of Shenzhen, China. As shown in FIG. 2, the temperature measurements taken with the thermometer gun showed that the heated PCM-laden CoolFlow™ material had a surface temperature that was always 1-2° F. lower than the temperature of the second piece of foam that was not treated with PCM.

Now that embodiments of the present invention have been shown and described in detail, various modifications and improvements thereon will become readily apparent to those skilled in the art. Accordingly, the spirit and scope of the present invention is to be construed broadly and not limited by the foregoing specification.

What is claimed is:

1. An absorbent article comprising:
    at least one layer including a foam with microPCM particles, wherein the foam comprises a resilient sheet of an open-cell foam comprising at least one of a polyether urethane foam, a polyester urethane foam, a foam rubber, or a high internal phase emulsion polyethylene foam, and the open-cell foam is liquid permeable.

2. The absorbent article of claim 1, wherein the at least one layer of the absorbent article is a topsheet, an acquisition layer, or an absorbent core.

3. The absorbent article of claim 1, further comprising a topsheet and an absorbent core, wherein the at least one layer of the absorbent article is a layer that is positioned between the topsheet and the absorbent core.

4. The absorbent article of claim 3, wherein the at least one layer serves as a carrier layer for the microPCM particles.

5. The absorbent article of claim 3, further comprising a backsheet.

6. The absorbent article of claim 1, further comprising a topsheet and an acquisition layer, wherein the at least one layer is positioned between the topsheet and the acquisition layer.

7. The absorbent article of claim 1, wherein the microPCM particles have a phase change temperature in the range of 98° F. to 99° F. (36° C. to 38° C.).

8. The absorbent article of claim 1, wherein the microPCM particles are embedded in the foam, are coated on the foam as an emulsion, or both embedded in and coated onto the foam.

9. The absorbent article of claim 8, wherein the microPCM particles are embedded in or are coated onto less than the entirety of the foam.

10. The absorbent article of claim 1, wherein the microPCM particles are made of paraffin wax that is encapsulated in an olefinic hard shell.

11. The absorbent article of claim 1, wherein the absorbent article is a diaper, underwear, a sanitary napkin, an incontinence product, or a hygienic product.

12. An absorbent article comprising:
    a topsheet, a backsheet, an absorbent core between the topsheet and backsheet, and a carrier layer, between the topsheet and the absorbent core, comprising a resilient sheet of an open-cell foam with microPCM particles, wherein the open-cell foam comprises at least one of a polyether urethane foam, a polyester urethane foam, a foam rubber, or a high internal phase emulsion polyethylene foam, and the open-cell foam is liquid permeable.

13. The absorbent article of claim 12, wherein the microPCM particles have a phase change temperature in the range of 98° F. to 99° F. (36° C. to 38° C.).

14. The absorbent article of claim 12, wherein the microPCM particles are embedded in the foam, are coated on the foam as an emulsion, or both embedded in and coated onto the foam.

15. The absorbent article of claim 14, wherein the microPCM particles are embedded in or are coated onto less than the entirety of the foam.

16. The absorbent article of claim 12, further comprising an acquisition layer positioned between the topsheet and the carrier layer.

17. The absorbent article of claim 12, wherein the microPCM particles are made of paraffin wax that is encapsulated in an olefinic hard shell.

18. The absorbent article of claim 12, wherein the absorbent article is a diaper, underwear, a sanitary napkin, an incontinence product, or a hygienic product.

* * * * *